(12) United States Patent
Kana et al.

(10) Patent No.: US 10,034,764 B2
(45) Date of Patent: Jul. 31, 2018

(54) INTERBODY FUSION DEVICE WITH LIPPED ANTERIOR PLATE AND ASSOCIATED METHODS

(75) Inventors: Richard Kana, Lexington, TX (US); Kevin Dunworth, Dripping Springs, TX (US); Luis Duarte, San Angelo, TX (US); Brian Burkinshaw, Pflugerville, TX (US); Mukund Gundanna, College Station, TX (US); Ryan Medema, Pflugerville, TX (US)

(73) Assignee: SpineSmith Partners, L.P., Austin, TX (US)

( * ) Notice: Subject to any disclaimer, the term of this patent is extended or adjusted under 35 U.S.C. 154(b) by 81 days.

(21) Appl. No.: 13/506,566

(22) Filed: Apr. 27, 2012

(65) Prior Publication Data
US 2012/0277873 A1   Nov. 1, 2012

Related U.S. Application Data

(63) Continuation-in-part of application No. 12/018,703, filed on Jan. 23, 2008, and a continuation-in-part of
(Continued)

(51) Int. Cl.
*A61F 2/44* (2006.01)
*A61B 17/86* (2006.01)
(Continued)

(52) U.S. Cl.
CPC ............ *A61F 2/4455* (2013.01); *A61F 2/447* (2013.01); *A61F 2/4465* (2013.01); *A61B 17/8042* (2013.01); *A61B 17/86* (2013.01); *A61F 2/30744* (2013.01); *A61F 2/4611* (2013.01); *A61F 2002/2817* (2013.01); *A61F 2002/2835* (2013.01); *A61F 2002/302* (2013.01); *A61F 2002/30131* (2013.01); *A61F 2002/30349* (2013.01); *A61F 2002/30352* (2013.01); *A61F 2002/30355* (2013.01); *A61F 2002/30372* (2013.01); *A61F 2002/30373* (2013.01);
(Continued)

(58) Field of Classification Search
CPC ........ A61F 2/4455; A61F 2/4465; A61F 2/44; A61F 2002/4475; A61F 2/4611
USPC .................... 623/17.11–17.16; 606/295, 296
See application file for complete search history.

(56) References Cited

U.S. PATENT DOCUMENTS 6,413,259 B1 *   7/2002   Lyons et al. .................. 606/295
7,232,463 B2 *   6/2007   Falahee ...................... 623/17.11
(Continued)

Primary Examiner — Julianna N Harvey
(74) Attorney, Agent, or Firm — Winstead PC

(57) ABSTRACT

A method and apparatus is provided for use in spinal fusion procedures. An interbody fusion device has a first piece that is a load bearing device designed to bear the axial loading from the end plates of adjacent vertebrae. A second piece of the interbody fusion device is a retention device whose function is to prevent migration of the load bearing device. One or more fasteners secure the retention device to the vertebrae above and below the load bearing device. The fasteners cause the end plates of the vertebrae to compress the end plates to the load bearing device to facilitate proper fusion. The second piece can be configured to include lips that abut the apothyseal rings during, with the plate including bores angled such that fasteners penetrate the apothyseal rings.

11 Claims, 22 Drawing Sheets

Related U.S. Application Data application No. 11/759,219, filed on Jun. 6, 2007, now Pat. No. 8,273,127.

(60) Provisional application No. 61/517,877, filed on Apr. 27, 2011, provisional application No. 60/981,414, filed on Oct. 19, 2007.

(51) Int. Cl.
*A61F 2/30* (2006.01)
*A61F 2/28* (2006.01)
*A61B 17/80* (2006.01)
*A61F 2/46* (2006.01)

(52) U.S. Cl.
CPC ............... *A61F 2002/30383* (2013.01); *A61F 2002/30387* (2013.01); *A61F 2002/30397* (2013.01); *A61F 2002/30482* (2013.01); *A61F 2002/30507* (2013.01); *A61F 2002/30509* (2013.01); *A61F 2002/30517* (2013.01); *A61F 2002/30578* (2013.01); *A61F 2002/30604* (2013.01); *A61F 2002/30607* (2013.01); *A61F 2002/30616* (2013.01); *A61F 2002/30774* (2013.01); *A61F 2002/30782* (2013.01); *A61F 2002/30904* (2013.01); *A61F 2002/4475* (2013.01)

(56) References Cited

U.S. PATENT DOCUMENTS

| | | | | |
|---|---|---|---|---|
| 7,594,931 | B2* | 9/2009 | Louis | A61B 17/86 606/247 |
| 7,875,061 | B2* | 1/2011 | Bolger | A61B 17/0206 606/280 |
| 2002/0082597 | A1* | 6/2002 | Fraser | A61F 2/30771 606/246 |
| 2004/0193269 | A1* | 9/2004 | Fraser | A61B 17/7059 623/17.11 |
| 2005/0085913 | A1* | 4/2005 | Fraser et al. | 623/17.11 |
| 2007/0250167 | A1* | 10/2007 | Bray | A61F 2/4465 623/17.11 |
| 2008/0269806 | A1* | 10/2008 | Zhang | A61F 2/4455 606/280 |
| 2008/0306596 | A1* | 12/2008 | Jones | A61F 2/4455 623/17.16 |
| 2009/0326580 | A1* | 12/2009 | Anderson | A61B 17/7059 606/246 |
| 2011/0040382 | A1* | 2/2011 | Muhanna | 623/17.11 |

* cited by examiner

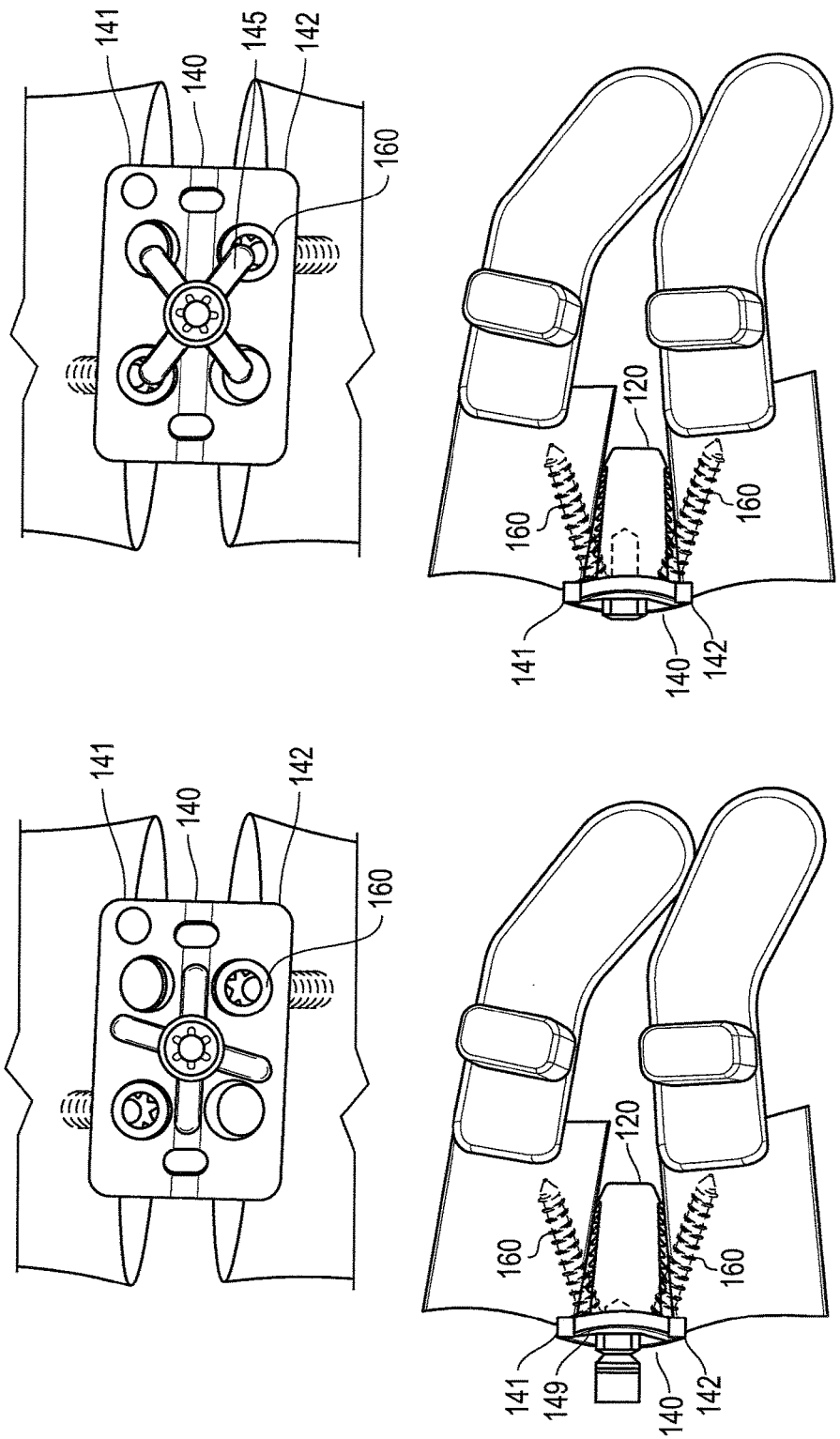

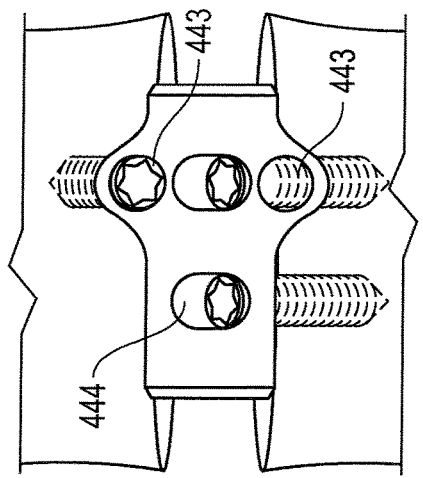 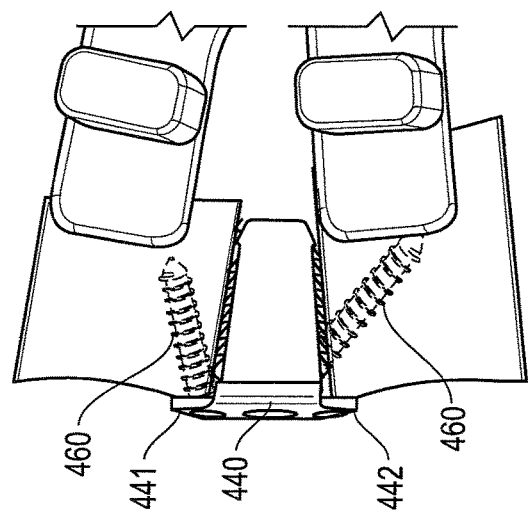
FIG. 29
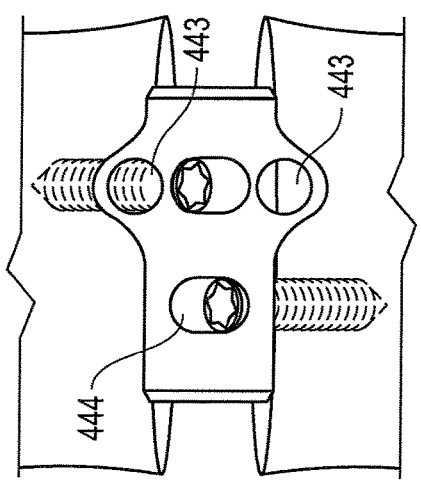 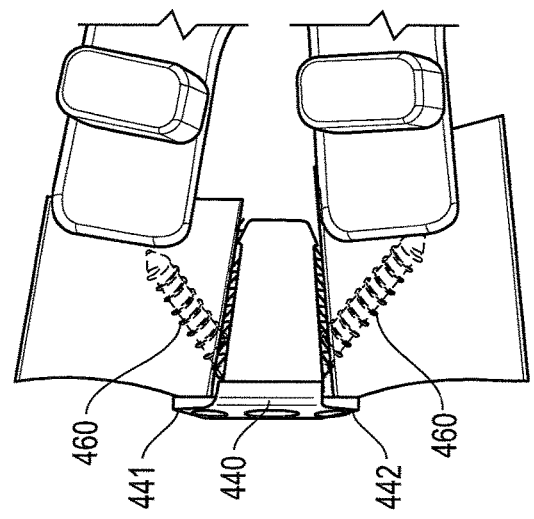
FIG. 28

INTERBODY FUSION DEVICE WITH LIPPED ANTERIOR PLATE AND ASSOCIATED METHODS

CLAIM TO EARLIER APPLICATION

This application claims priority to U.S. Provisional Patent Application No. 61/517,877, filed Apr. 27, 2011, and is a continuation-in-part of co-pending nonprovisional application Ser. No. 12/018,703, filed Jan. 23, 2008, which claims priority to provisional application Ser. No. 60/981,414, filed Oct. 19, 2007, and is a continuation-in-part of co-pending nonprovisional application Ser. No. 11/759,219, filed March, 2007, all of which are incorporated herein by reference

FIELD OF THE INVENTION

This invention relates to the field of spinal fusion. In particular, this invention is drawn to spinal fusion devices and associated methods.

BACKGROUND OF THE INVENTION

The spine can be considered to be a series of movable segments made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent future damage.

One procedure that is often used to treat back pain or spinal damage is spinal fusion. Spinal fusion is a surgical technique used to combine two or more adjacent vertebrae. Supplemental bone tissue is used in conjunction with the patient's natural osteoblastic processes in a spinal fusion procedure. Spinal fusion is used primarily to eliminate back pain caused by the motion of the damaged vertebrae by immobilizing adjacent vertebrae. Conditions for which spinal fusion might be done include degenerative disc disease, treatment of a spinal tumor, a vertebral fracture, scoliosis, degeneration of the disc, spondylolisthesis, or any other condition that causes instability of the spine.

One problem with prior art spinal fusion techniques relates to device migration. For example, prior to complete bone fusion, a fusion device may migrate from the desired position. In examples where bone screws are used, the insertion and tightening of the bone screws tends to cause device migration. Another problem with typical prior art fusion techniques is that fusion devices, or associated plates or fasteners, protrude from the spine, causing discomfort, damage, or danger to surrounding vascular or neurological tissues.

There is therefore a need for spinal fusion devices and related spinal fusion procedures that adequately treats degenerative disc disease and other spinal conditions, while providing improvements over the prior art.

SUMMARY OF THE INVENTION

An apparatus of the invention provides a spinal fusion device including a fusion bearing device configured to fit between two adjacent vertebrae, and a retention device configured to be secured to at least one of the adjacent vertebrae to prevent migration of the fusion bearing device, wherein the retention device has a height that is less than the height of the fusion bearing device.

One embodiment of an interbody fusion device includes a first piece configured to be placed between adjacent vertebrae, a second piece configured to at least partially fit within the first piece when the first piece is inserted between adjacent vertebrae, and one or more fastening devices for securing the second piece to at least one of the adjacent vertebrae.

Another embodiment of the invention provides a spinal fusion device including a fusion bearing device configured to fit between two adjacent vertebrae, a retention device configured to prevent migration of the fusion bearing device, wherein the retention device has a height that is less than the height of the fusion bearing device, one or more fasteners coupled to the retention device to compress the two adjacent vertebrae to the fusion bearing device.

Another embodiment of the invention provides a method of fusing adjacent vertebrae including providing an interbody fusion device, inserting the interbody fusion device between two adjacent vertebrae, providing a retention device configured to fit within the interbody fusion device, sliding the retention device into the interbody fusion device, and securing the retention device to at least one of the adjacent vertebrae.

The inventors have discovered that the fusion device as depicted in FIGS. 1-11, for example, which have zero profile anteriorly, can be improved upon for some applications. When such a fusion device is to be implemented in a patient using minimally invasive surgical techniques, there can be difficulty for the surgeon due to space and viewing limitations to affix the retention device to vertebrae because a large angle of approach is needed to screw in fasteners that enter the vertebrae, for example at a 35 degree angle. This angle can make screwing the fasteners in because of special flexible screw drivers must be used, for example, to enable a surgeon to drive the fasteners into the vertebrae. Likewise, long fasteners must be used because the portion of the vertebrae being accessed is relatively soft as compared to the bone of the apophyseal rings. Thus, other embodiments were developed by the inventors to create an anterior plate (retention device) that was still low profile but which permitted the fasteners to use the apophyseal rings for the fasteners, thereby permitting a lower angle of approach and shorter screws relative to the device of FIGS. 1-11. The improvement includes use of an anterior plate that has at least one lip that abuts and overhangs an apophyseal ring during use. The lip allows use of fasteners that can be driven through the apophyseal plates at an angle that need not be as great as an angle for the device of FIGS. 1-11. The lip is designed to abut the ring so that only a portion of the anterior plate is not zero profile. Furthermore, the anterior plate is a separate piece thereby permitting the load bearing component to be packed in situ with bone graft material. Likewise, the new anterior plate can be reversible. Moreover, the new anterior plate can be configured to permit multiple angles of approach in certain embodiments.

In this regard, another embodiment of this invention is a spinal fusion device comprising: a fusion component configured to have a zero profile and to fit between two adjacent vertebrae; and a separate anterior plate configured to couple to the fusion component, the anterior plate configured with bores to receive fasteners, wherein the anterior plate includes a lip that includes a portion with at least one bore to fit a fastener and permit a fastener to contact apophyseal ring bone during use and wherein the portion of the anterior plate that is not a lip has a zero profile anteriorly; fasteners that couple to bores. The spinal fusion device can be configured so that the fusion component generally conforms to the contour of the adjacent vertebrae, can be configured so that fasteners are bone screws, can be configured so that the fusion component has a hollow center portion adapted to receive a material to enhance spinal fusion, can be configured so that the component bearing device and the anterior plate have a mating tongue and groove elements, can further comprise an anti-backout mechanism that couples to the anterior plate to prevent fastener migration during use, can be configured so that the fusion component is U-shaped (horseshoe shaped), can be configured so that a portion of the anterior plate has a height that is less than the height of the U-shaped component, can be configured so that the anterior plate has a single lip, can be configured so that the anterior plate has two lips each on opposite portions of the anterior plate, can be configured so that the anterior plate is reversible so that the plate can be used in two opposite configurations, can be configured so that a portion of the superior part of the anterior plate is a lip and wherein a portion of the inferior part of the anterior plate is a lip and wherein each lip does not extend the entire length of the anterior plate, can be configured so that a portion of the superior part of the anterior plate is a lip and wherein a portion of the inferior part of the anterior plate is a lip and wherein each lip does not extend the entire length of the anterior plate, and wherein both lips are positioned in the central portion (middle) of the anterior plate, and including but not limited to any combination thereof.

In another broad respect, this invention is a method of fusing adjacent vertebrae, comprising: providing a spinal fusion device which comprises: a fusion component configured to have a zero profile and to fit between two adjacent vertebrae; and a separate anterior plate configured to couple to the fusion component, the anterior plate configured with bores to receive fasteners, wherein the anterior plate includes a lip that includes a portion with at least one bore to fit a fastener and permit a fastener to contact apophyseal ring bone during use and wherein the portion of the anterior plate that is not a lip has a zero profile anteriorly; fasteners that couple to bores; inserting the fusion component between two adjacent vertebrae; coupling the anterior plate to the fusion component; and driving the fasteners into the vertebrae through the bores to secure the anterior plate to the fusion component and to pull the vertebrae toward the anterior plate and the fusion component.

In another broad respect, this invention is a method of manufacturing a kit for spinal fusion, comprising: providing a fusion component configured to have a zero profile and to fit between two adjacent vertebrae; and providing a separate anterior plate configured to couple to the fusion component, the anterior plate configured with bores to receive fasteners, wherein the anterior plate includes a lip that includes a portion with at least one bore to fit a fastener and permit a fastener to contact apophyseal ring bone during use and wherein the portion of the anterior plate that is not a lip has a zero profile anteriorly; fasteners that couple to bores.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which:

FIGS. 12-22 show embodiments of the device of this invention using an anterior plate having two opposing lips that facilitate fastener implantation at lower angles of approach and through the apophyseal rings.

FIGS. 26-30 show embodiments of the invention wherein the anterior plate has two lips on opposing sides but wherein the plate is zero profile in the other portions of each opposing side.

DETAILED DESCRIPTION

The present invention relates to spinal fusion implants and related spinal fusion procedures for use in cervical and lumbar applications. One type of spinal fusion is interbody fusion. Typically, an interbody fusion procedure places a bone graft between the vertebra in the area normally occupied by an intervertebral disc. In preparation for a spinal fusion procedure, the intervertebral disc is removed entirely. A device may be placed between the vertebra to maintain spine alignment and disc height. Fusion then occurs between the endplates of the vertebrae. In some examples, fusion is augmented by a process called fixation, meaning the placement of screws; rods or plates to stabilize the vertebra to facilitate bone fusion. The present invention provides an interbody fusion device that overcomes problems found in the prior art.

Generally, the present invention provides a two piece interbody fusion device that may be used with anterior lumbar interbody fusion (ALIF). In one example, a first piece of the interbody fusion device is a U-shaped load bearing device that is designed to bear the axial loading from the end plates of adjacent vertebrae. A second piece of the interbody fusion device is a retention device whose function is to prevent migration of the load bearing device. One or more fasteners, such as bone screws secure the retention device to the vertebrae above and below the load bearing device. The fasteners cause the end plates of the vertebrae to compress the end plates to the load bearing device to facilitate proper fusion. If desired, the fasteners may include an anti-backout mechanism.

Figure 1:
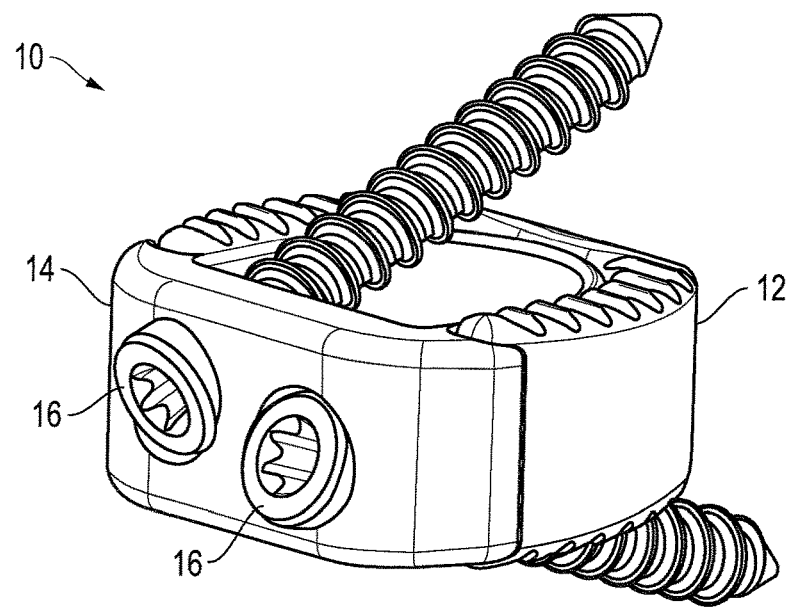
FIG. 1 is an isometric view of one example of an interbody fusion device of the present invention.

FIG. 1 is an isometric view of one example of an interbody fusion device of the present invention. FIG. 1 shows an interbody fusion device 10. The interbody fusion device 10 includes a load bearing device 12, a retention device 14, and two bone screws 16, each of which are described in more detail below.

Figure 2:
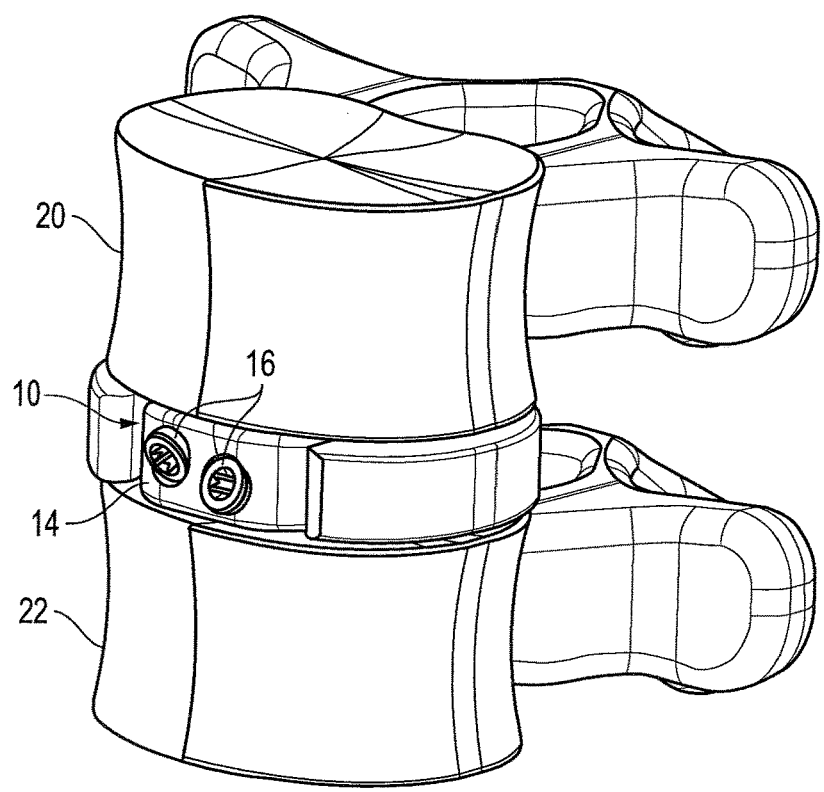
FIG. 2 is an isometric diagram of the interbody fusion device shown in FIG. 1 installed between the end plates of two adjacent vertebrae.

FIG. 2 is an isometric diagram of the interbody fusion device 10 shown in FIG. 1 installed between the end plates of two adjacent vertebrae 20 and 22 to facilitate the fusion of the vertebrae 20 and 22. The interbody fusion device 10 provides load bearing support as well as the proper spacing between the vertebrae 20 and 22 while fusion of the vertebrae takes place. As described in more detail below, the interbody fusion device 10 is positioned between the end plates of the vertebrae 20 and 22 within the vertebral body in the area usually occupied by the intervertebral disc.

Figure 3:
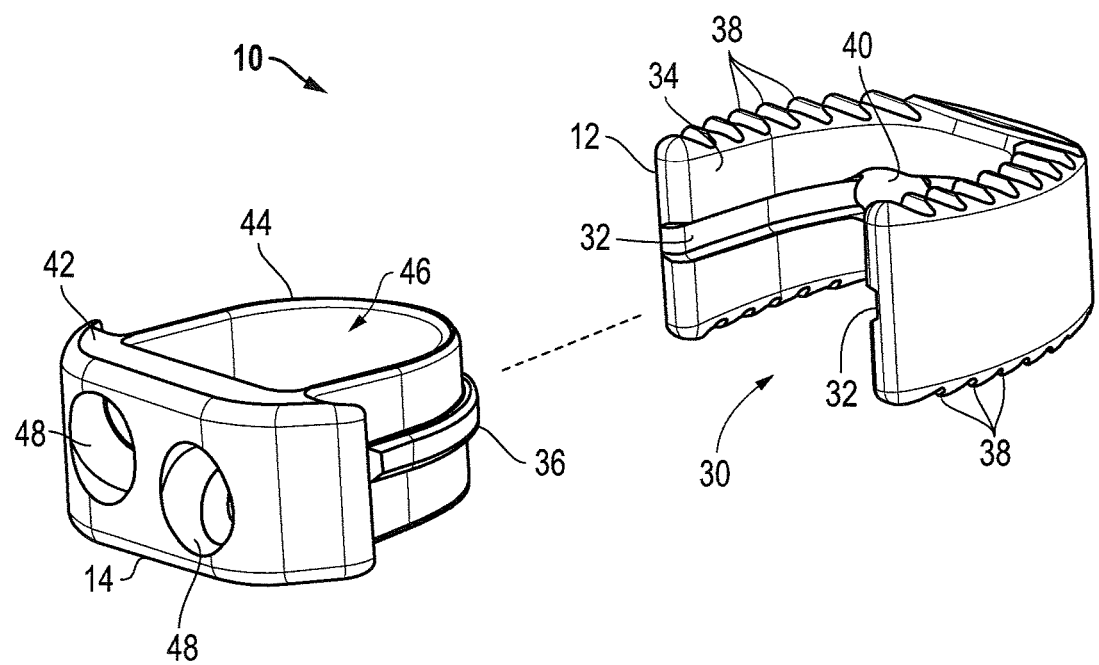
FIG. 3 is an exploded view of an interbody fusion device, showing a load bearing device and a retention device.

FIGS. 3-6 are views illustrating various details of one example of an interbody fusion device of the present invention. FIG. 3 is an exploded view of the interbody fusion device 10, showing the load bearing device 12 and the retention device 14 separately. The load bearing device 12 is a generally U-shaped device having an open end 30 that is configured to receive the retention device 14 (described below). A groove 32 is formed around the interior surface 34 of the load bearing device 12. A corresponding tongue 36 is formed around the outside surface of the retention device 14 such that, when the retention device 14 is inserted within the open end 30 of the load bearing device 12, the tongue 36 and groove 32 tend to hold the retention device 14 in a desired position, relative to the load bearing device 12.

The load bearing device 12 also includes a plurality of ridges 38 formed on the top and bottom ends of the device 12. The ridges 38 are angled and come to a point in such a way that the ridges 38 help to hold the load bearing device 12 to the end plates of the vertebrae to reduce the chance of anterior migration of the implant. If desired, one or more openings 40 can be formed in the load bearing device 12 to facilitate instrumentation device. In the example shown in FIG. 3, two openings 40 are formed on opposite sides of the load bearing device 12 (the second opening 40 is hidden in FIG. 3). An implant holder can be used to insert the load bearing device 12 into a vertebral body using the openings 40.

The retention device 14 has a front portion 42 and a rear portion 44 that, together, form a hollow body 46. The hollow body 46 provides a relatively large graft volume, compared to a typical ALIF allograft. Prior to insertion into the load bearing device 12, the hollow body 46 of the retention device 14 can be filled with a prepared material that will help to facilitate fusion of the vertebrae (see FIGS. 9-10). Examples of a material include allograft bone, autograft bone, bone marrow, bone morphonogenic protein (BMP), Autologous Stem Cells, etc., to facilitate fusion through opening 46.

The retention device 14 is shaped to such that it will fit within the open end 30 of the load bearing device 12. In the example shown in FIG. 3, two holes 48 are formed in the front portion 42, and are adapted to received fasteners, such as bone screws, pegs, etc. One of the holes 48 is angled down, and the other hole 48 is angled up, such that a first fastener can be secured to the vertebra above the interbody fusion device 10, and a second fastener can be secured to the vertebra below the interbody fusion device 10 (described in more detail below).

Figure 4:
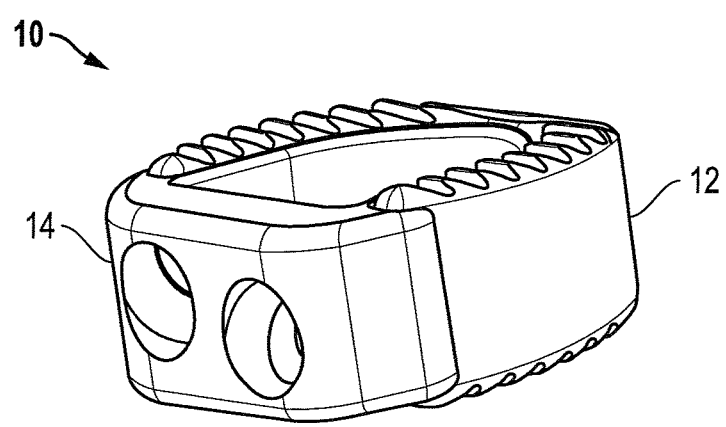
FIG. 4 is an isometric diagram of the interbody fusion device shown in FIG. 3 with the retention device inserted into the load bearing device.

FIG. 4 is an isometric diagram of the interbody fusion device 10 shown in FIG. 3 with the retention device 14 inserted into the load bearing device 12. As shown, the retention device 14 fits within the load bearing device 12. The resulting assembly provides a load bearing structure that is safely secured in place without any fasteners having to be placed directly into the load bearing device 12. FIG. 4 also illustrates that the height of the retention device 14 is less than the height of the load bearing device 12. As a result, all of the load on the vertebrae will be placed on the load bearing device 12, and not on the retention device 14. At the same time the load bearing device 12 is securely is the position desired by the surgeon. In some prior art devices, the fastening mechanisms (e.g., cervical plates with screws, spacers held in place by off-set screws, etc.), will bear some of the load, increasing the likelihood of device failure or migration. In addition, with typical prior art devices, a spacer is likely to migrate or twist slightly as bone screws are tightened by the surgeon. With the interbody fusion device 10 of the present invention, the load bearing structure will remain stationary, even as bone screws are tightened to secure the retention device in place.

Figure 5:
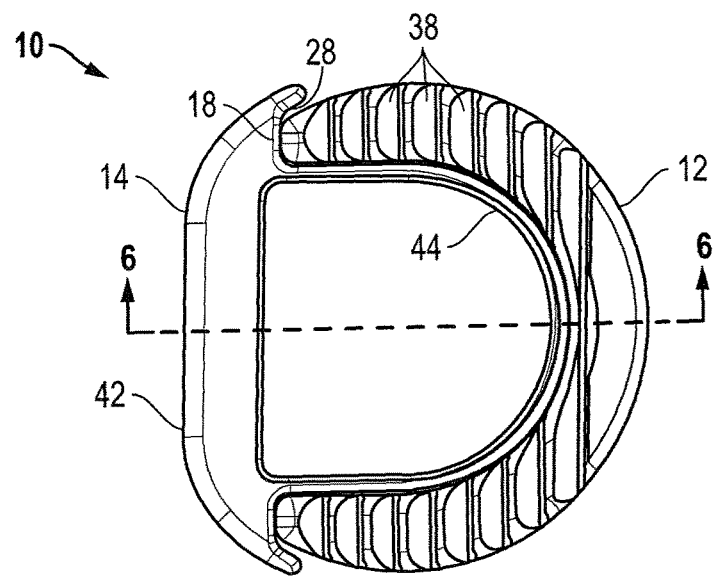
FIG. 5 is a top view of the assembled interbody fusion device shown in FIG. 4.

FIG. 5 is a top view of the assembled interbody fusion device 10 shown in FIG. 4. As shown, when the load bearing device 12 and retention device 14 are put together, the interbody fusion device 10 has a generally round profile that substantially fits within a vertebral body (shown in more detail below). FIG. 5 also illustrates how the load bearing device 12 is securely held in place by the retention device 14, such that anterior and lateral migration is prevented. Also note that that trailing edges 18 of the load bearing device 12 are nested and contained in pockets 28 formed in the retention device 14. This further secures the load bearing device 12 in place.

Figure 6:
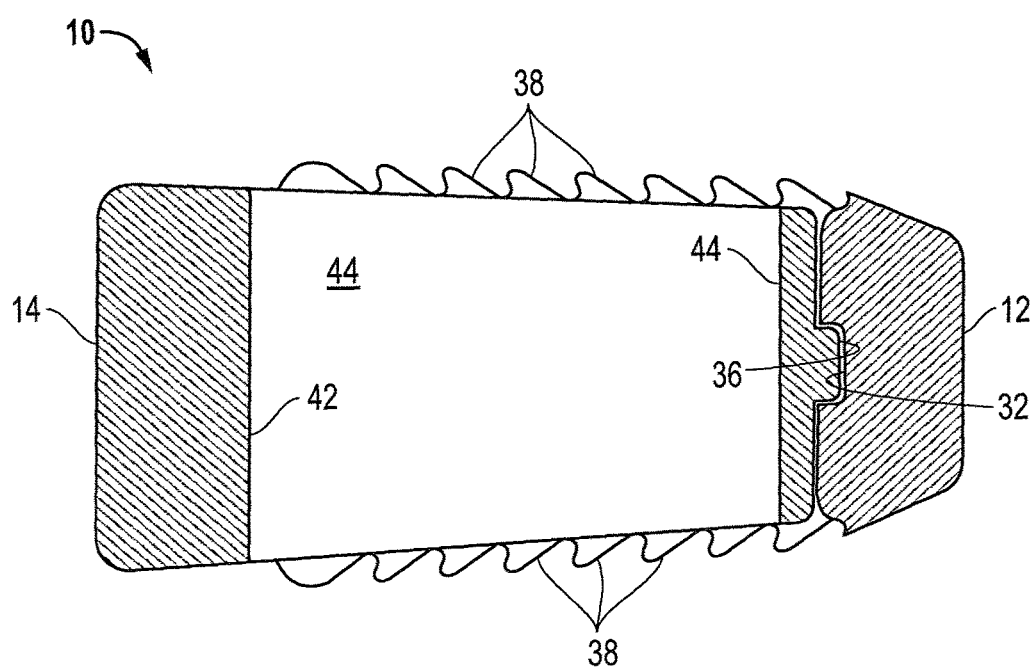
FIG. 6 is a sectional diagram taken along line 6-6 of FIG. 5.

FIG. 6 is a sectional diagram taken along line 6-6 of FIG. 5. FIG. 6 shows the retention device 14, including the front portion 42 and the rear portion 44, which forms the hollow body 46. The tongue 36 of the retention device 14 fits within the groove 32 of the load bearing device 12. FIG. 6 also more clearly illustrates that the height of the load bearing device 12 is greater than the height of the retention device 14. As a result, the load bearing device 12 will be the structure (primarily, the ridges 38) that engages the end plates of the vertebrae, thus supporting the axial loading of the vertebrae.

Figure 7:
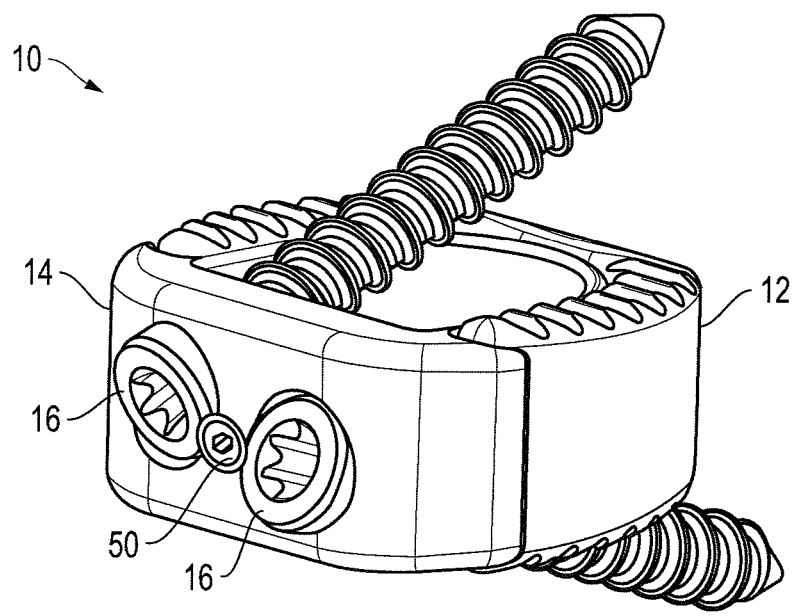
FIG. 7 is an isometric diagram of an interbody fusion device utilizing an anti-backout mechanism.

As mentioned above, the bone screws 16 may include an anti-backout mechanism. FIG. 7 is an isometric diagram of the interbody fusion device 10 utilizing an anti-backout mechanism. In this example, the anti-backout mechanism is comprised of a set screw 50, which can be screwed into the front portion of the retention device 14. The set screw in this example includes a driver socket for receiving a driver, which may be used by a surgeon to tighten the set screw 50. Of course, any desired type of anti-backout device may also be used.

As was shown in FIG. 2, an interbody fusion device of the present invention is intended to be installed between the end plates of two adjacent vertebrae to facilitate the fusion of the vertebrae. FIGS. 8-11 further illustrate the installation of an interbody fusion device of the present invention between adjacent vertebrae.

Figure 8:
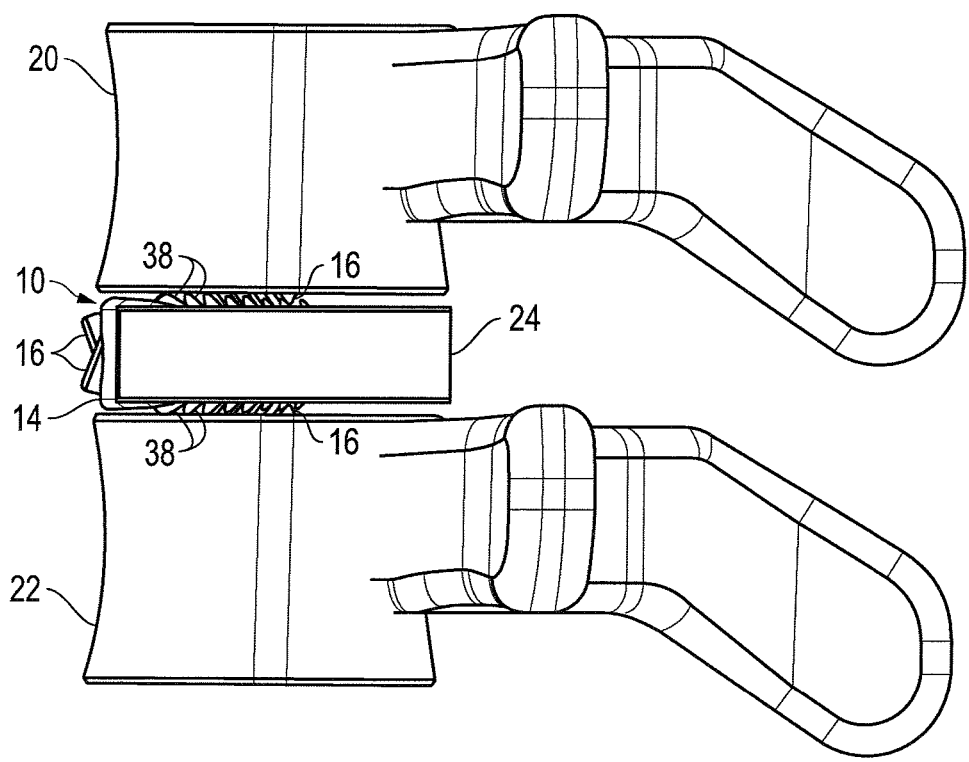
FIG. 8 is a side view of the interbody fusion device and vertebrae shown in FIG. 2.

FIG. 8 is a side view of the interbody fusion device 10 and vertebrae shown in FIG. 2. As shown in FIG. 8, the interbody fusion device 10 has a zero-profile anteriorly. In other words, the interbody fusion device 10 has a shape (e.g., see FIG. 5) in the axial plane that substantially fits within the perimeter defined by the vertebrae. In typical prior art devices, a cervical plate, or similar structure, is affixed to the side of the vertebrae, creating an extending profile that can cause discomfort, or damage to nearby tissue. Also note from FIG. 8 that the interbody fusion device 10 (not including the bone screws 16) also does not extend beyond (above or below) the end plates of the vertebrae.

Prior to the insertion of the interbody fusion device 10, the intervertebral disc is removed, so the interbody fusion device 10 can be place between the vertebrae 20 and 22. In one example, a window is cut in the disc annulus 24. Next, portions of the nucleus pulpous 26 (FIGS. 9, 10) are removed so that the interbody fusion device 10 can fit between the vertebrae 20 and 22 as shown in the figures.

Figure 9:
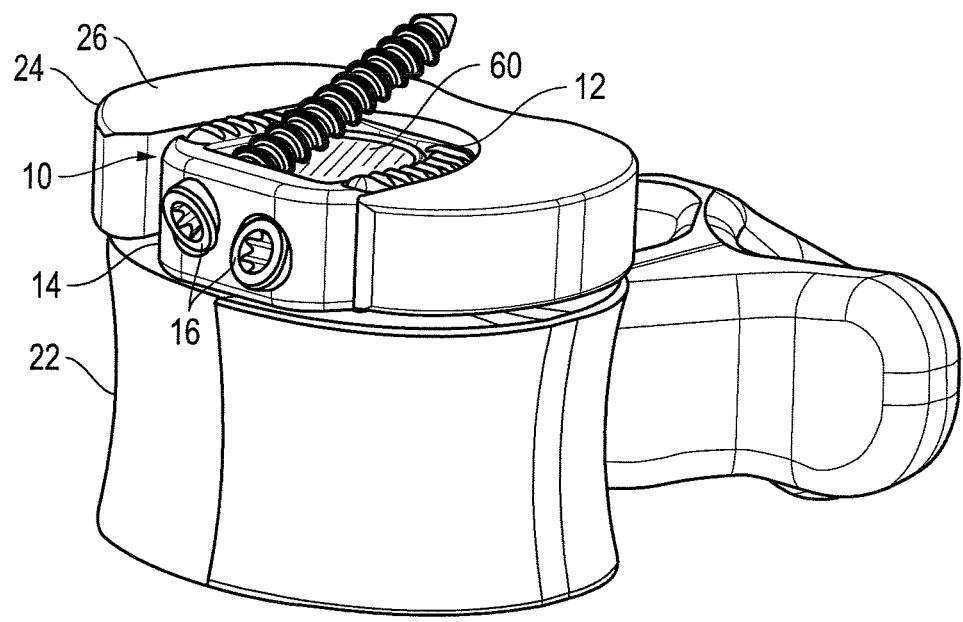
FIG. 9 is an isometric view similar to FIG. 2, but with the upper vertebra removed.
Figure 10:
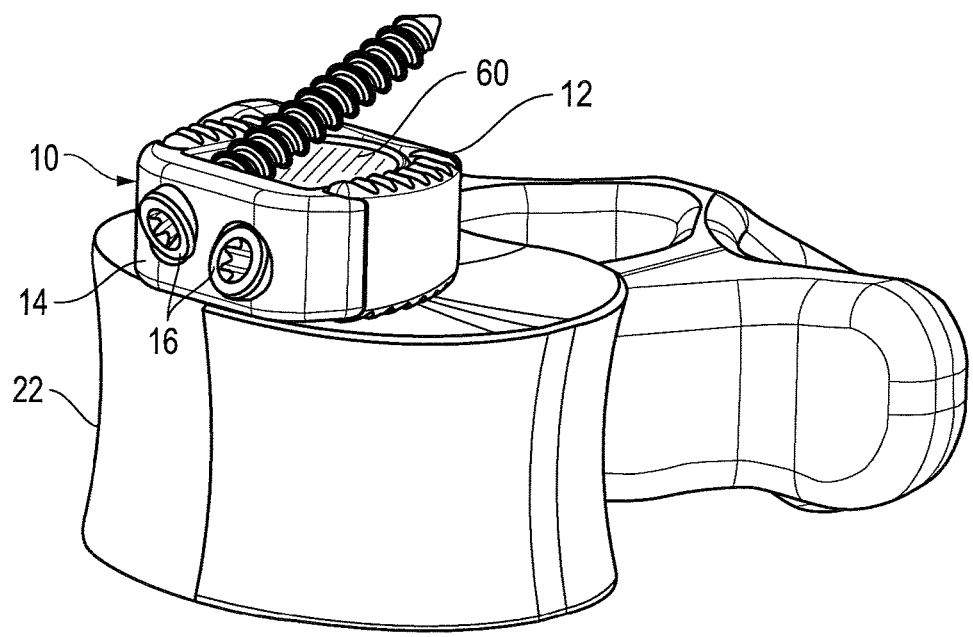
FIG. 10 is an isometric view similar to FIG. 9, but with the disc annulus and nucleus pulpous removed.
Figure 11:
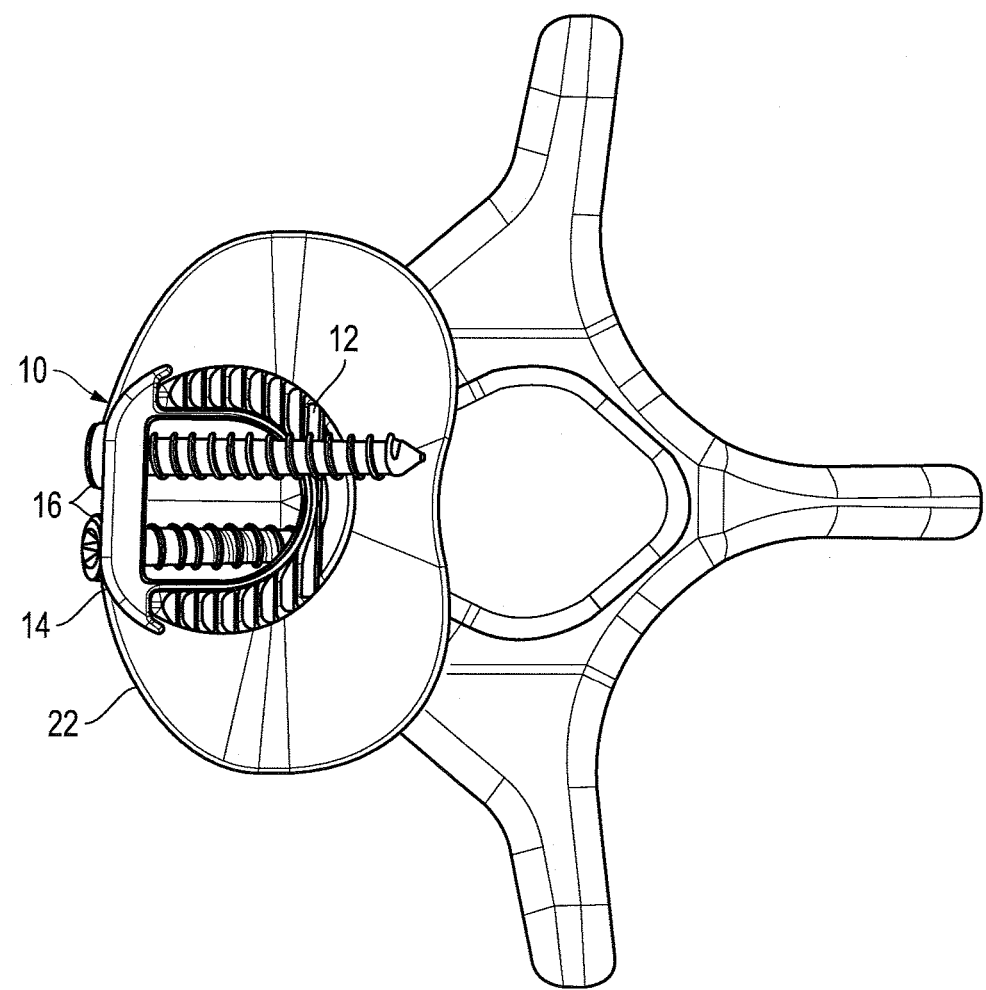
FIG. 11 is a top view of the interbody fusion device and vertebral body shown in FIG. 10.
Figure 12:
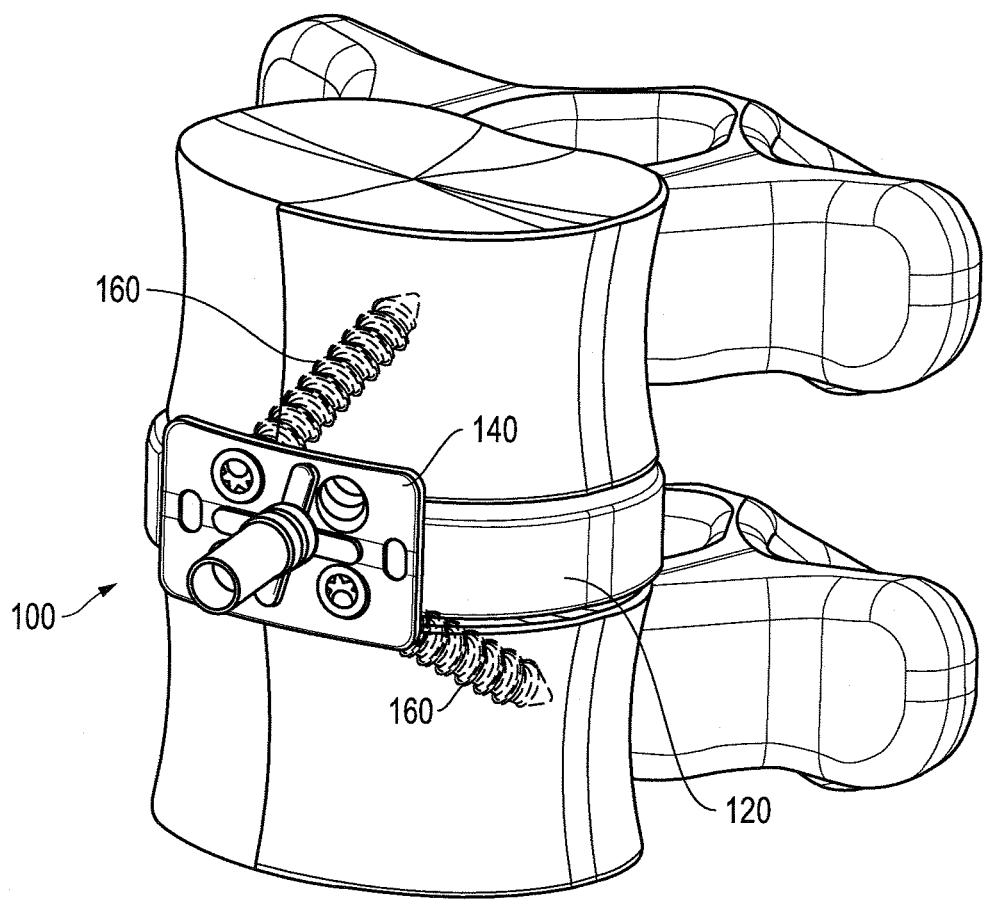
Figure 13:
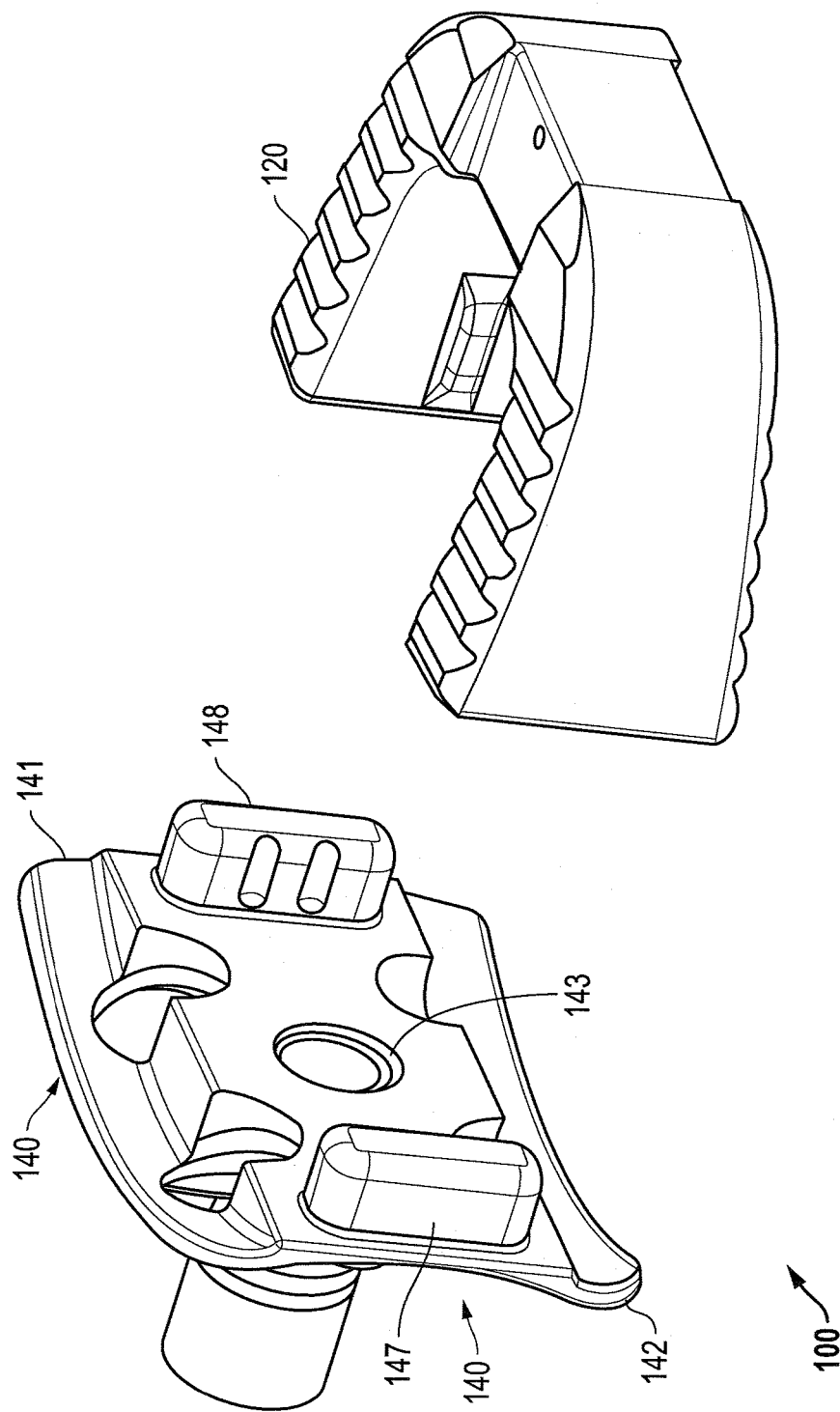
Figure 16:
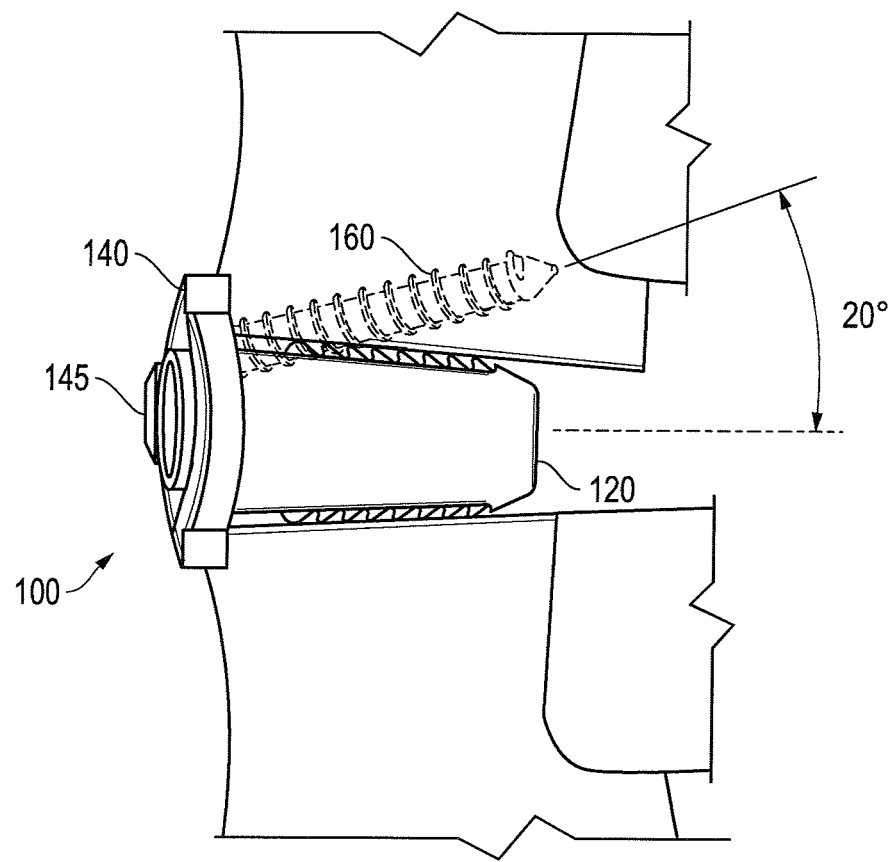
Figure 17:
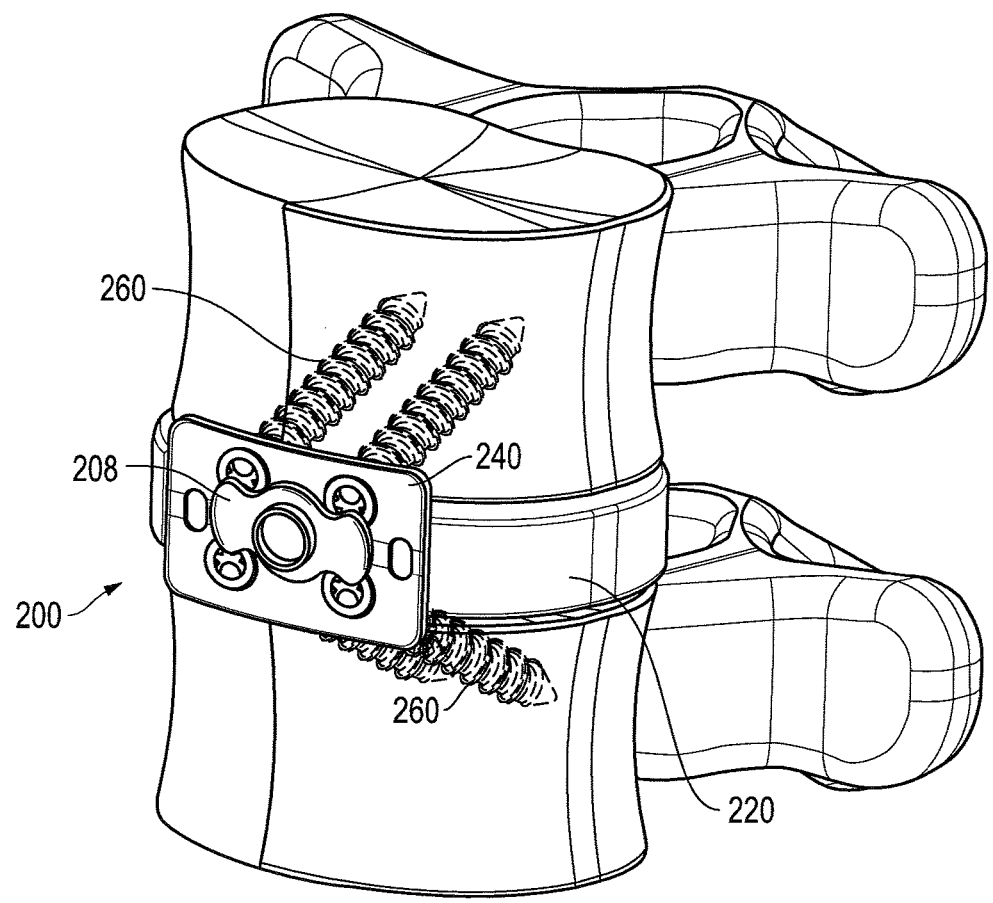
Figure 18:
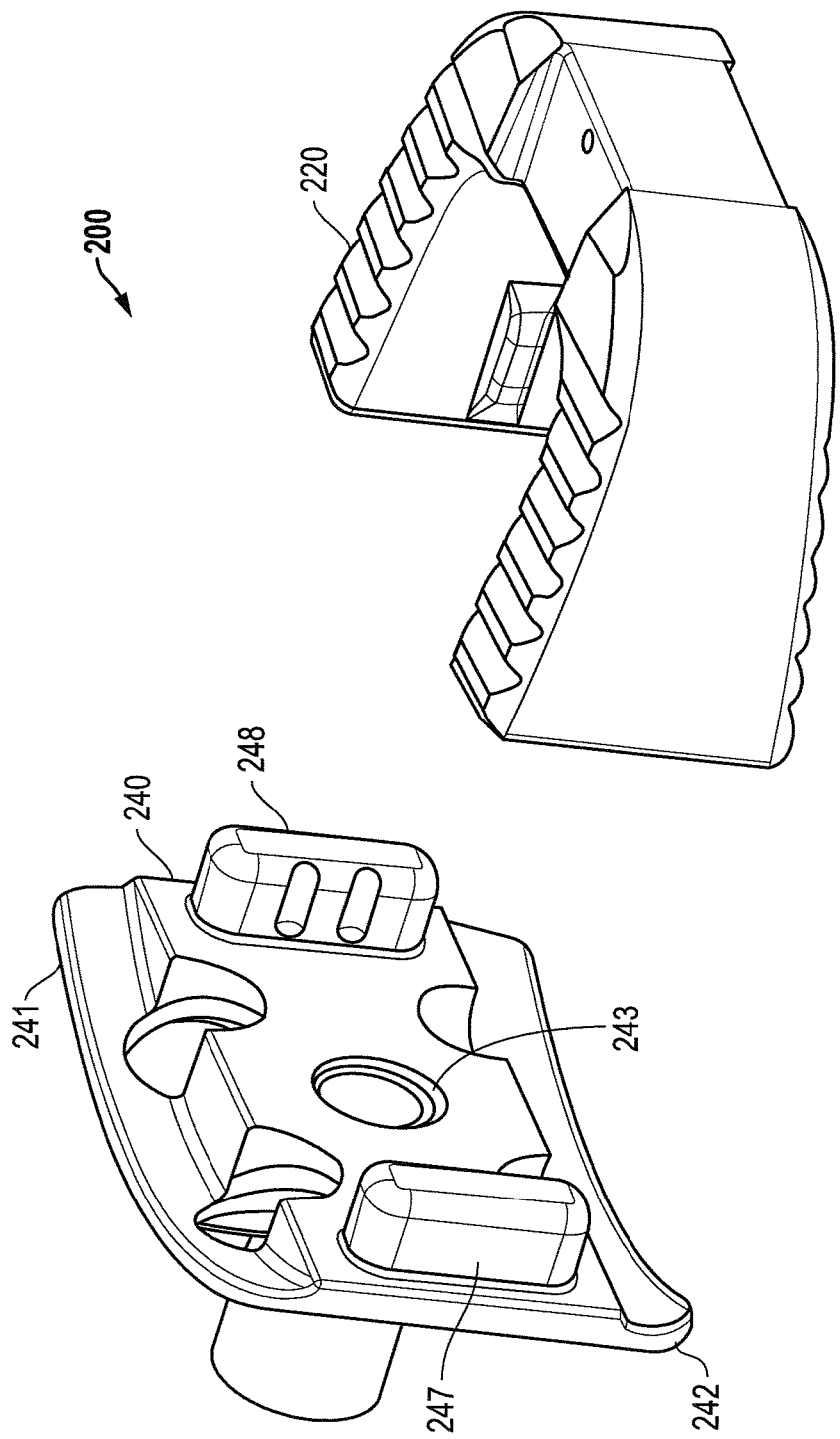
Figure 19:
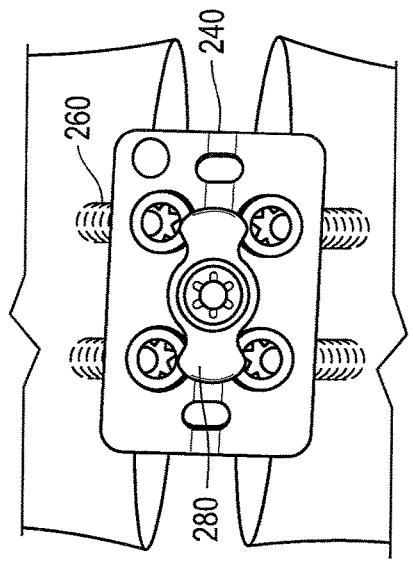
Figure 20:
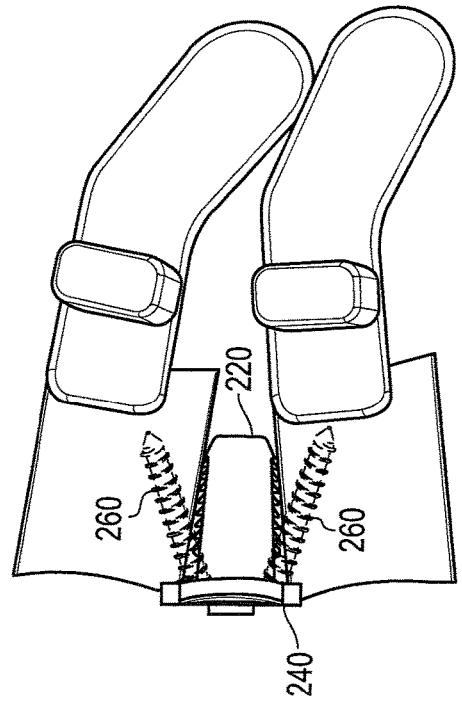
Figure 21:
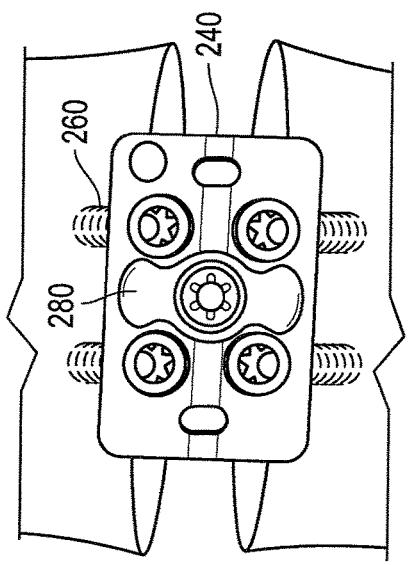
Figure 22:
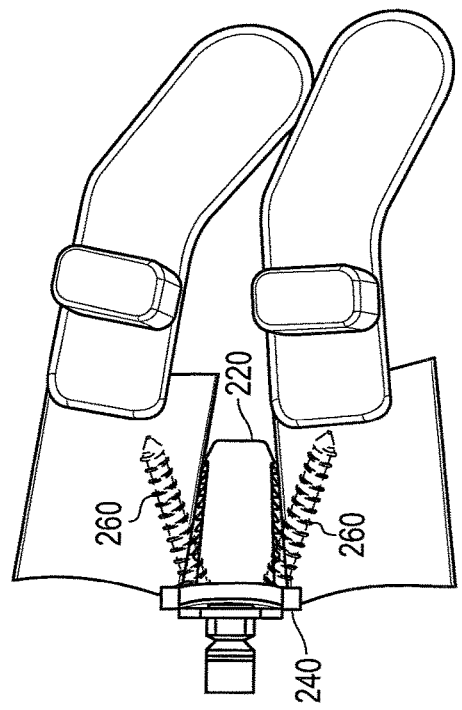

FIG. 9 is an isometric view similar to FIG. 2, but with the vertebra 20 removed to illustrate how the interbody fusion device 10 is positioned relative to the vertebrae and disc annulus 24. FIG. 9 shows the disc annulus 24 with a portion removed to allow the interbody fusion device 10 to be inserted. FIG. 9 also shows the remaining nucleus pulpous 26 surrounding the interbody fusion device 10. FIG. 10 is an isometric view similar to FIG. 9, but with the disc annulus 24 and nucleus pulpous 26 removed to further illustrate how the interbody fusion device 10 is positioned relative to the vertebrae and disc annulus 24. FIGS. 9 and 10 also include shading, which represents fusion material 60, described above. FIG. 11 is a top view of the interbody fusion device 10 and vertebral body shown in FIG. 10. Note that, for clarity, the material 60 is not shown in FIG. 11.

Another embodiment of this invention is depicted in FIGS. 12-16, which are particularly adapted for fusion of L2-L5 and S1 and in particular L4/L5 and L5/S1, which create challenging access for the surgeon to place screws in the endplates. Due to sharper curve/angle of the vertebrae column, the embodiment shown in FIGS. 12-16 provides through the anterior plate 140 for a decreased angle of entry for the fasteners, e.g. a 20 degree angle instead of 35 degrees for the device of FIGS. 1-11. This decreased angle is provided by the lips 141, 142 of the anterior retention device 140, which abut the respective vertebrae's apophyseal rings. That is, the apophyseal ring approach allows for a decreased angle of the fasteners into the bone.

The embodiment of this invention 100 depicted in FIGS. 12-16 includes a fusion bearing component 120, an anterior anterior plate 140, and from two to four fasteners 160.

The term "anterior plate" in general has the same meaning as "retention device" as used herein. The anterior plate is also sometimes referred to as a face plate or rescue plate. In certain embodiments the anterior plate includes one or two lips. The term "fusion component" generally has the same meaning as "fusion bearing device." The use of the term component is used to differentiate the piece from the spinal fusion device as a whole. The term "lip" as used herein for the portion of the anterior plate that abuts the apophyseal ring can also be referred to as a "ledge."

The spinal fusion device 100 has an upper lip 141 and lower lip 142 that abut the apophyseal ring during use. The anterior plate 140 includes from two to four bores that permit the fasteners 160 access to the bone to secure the spinal fusion device 100 into place. The anterior plate also includes a threaded bore 143 configured for receipt of a locking mechanism 145. The locking mechanism covers all screw bores in one motion when deployed. FIG. 14 shows the lips 141, 142 in more detail. The anterior plate 140 (which can also be referred to herein as a retention device) includes male couplers 147, 148 that are configured to slide into corresponding female coupling openings/bores (not shown) of the fusion component 120. The male couplers could also be tongue and groove mating surface. The anterior plate 140 includes a curvature 149 best seen in FIGS. 15 and 16 that forms a recess for the retention mechanism 170 to limit the anterior profile.

The embodiment of the invention shown in FIGS. 17-22 is similar to the embodiment of FIGS. 12-16. The spinal fusion device 200 of FIGS. 17-22 includes a fusion component 220, an anterior retention plate 240, from two to four fasteners 260, and a locking mechanism 280. The locking mechanism 280 has a generally rectangular shape that is sized and configured to partially cover all four fastener bores when deployed.

Figure 23:
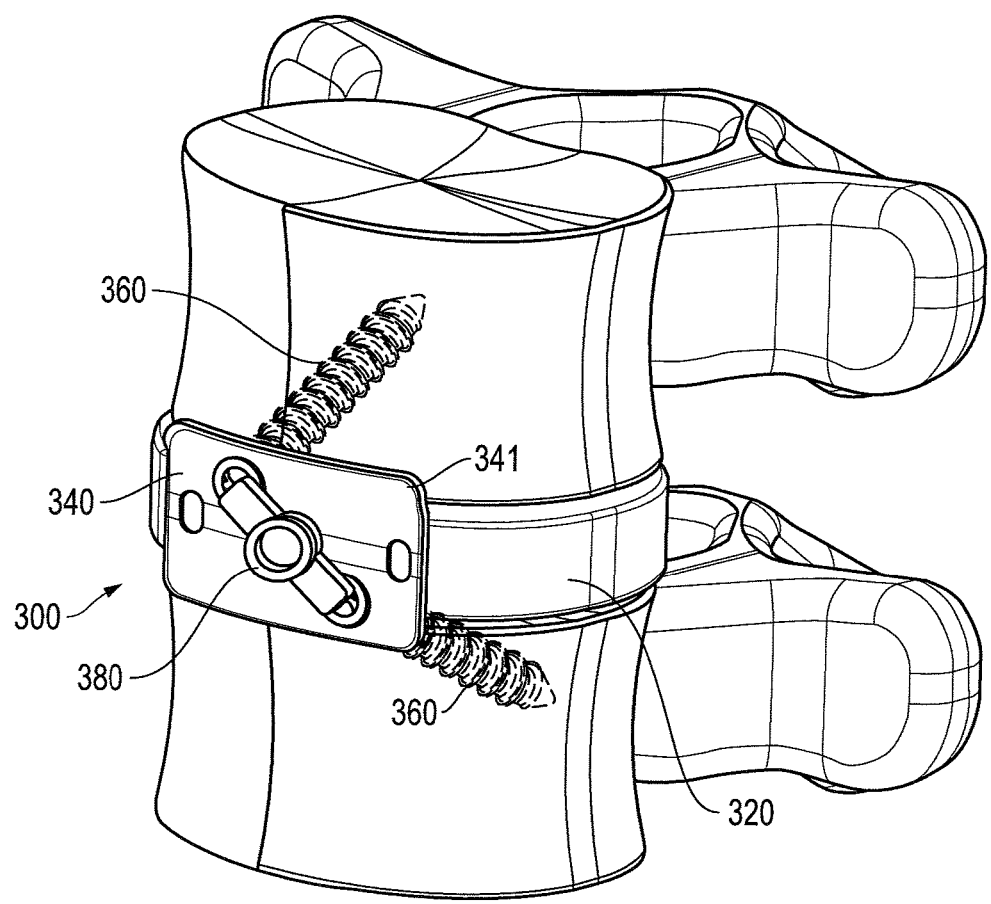
FIGS. 23-25 show embodiments of the invention using an anterior plate that has a single lip.
Figure 24:
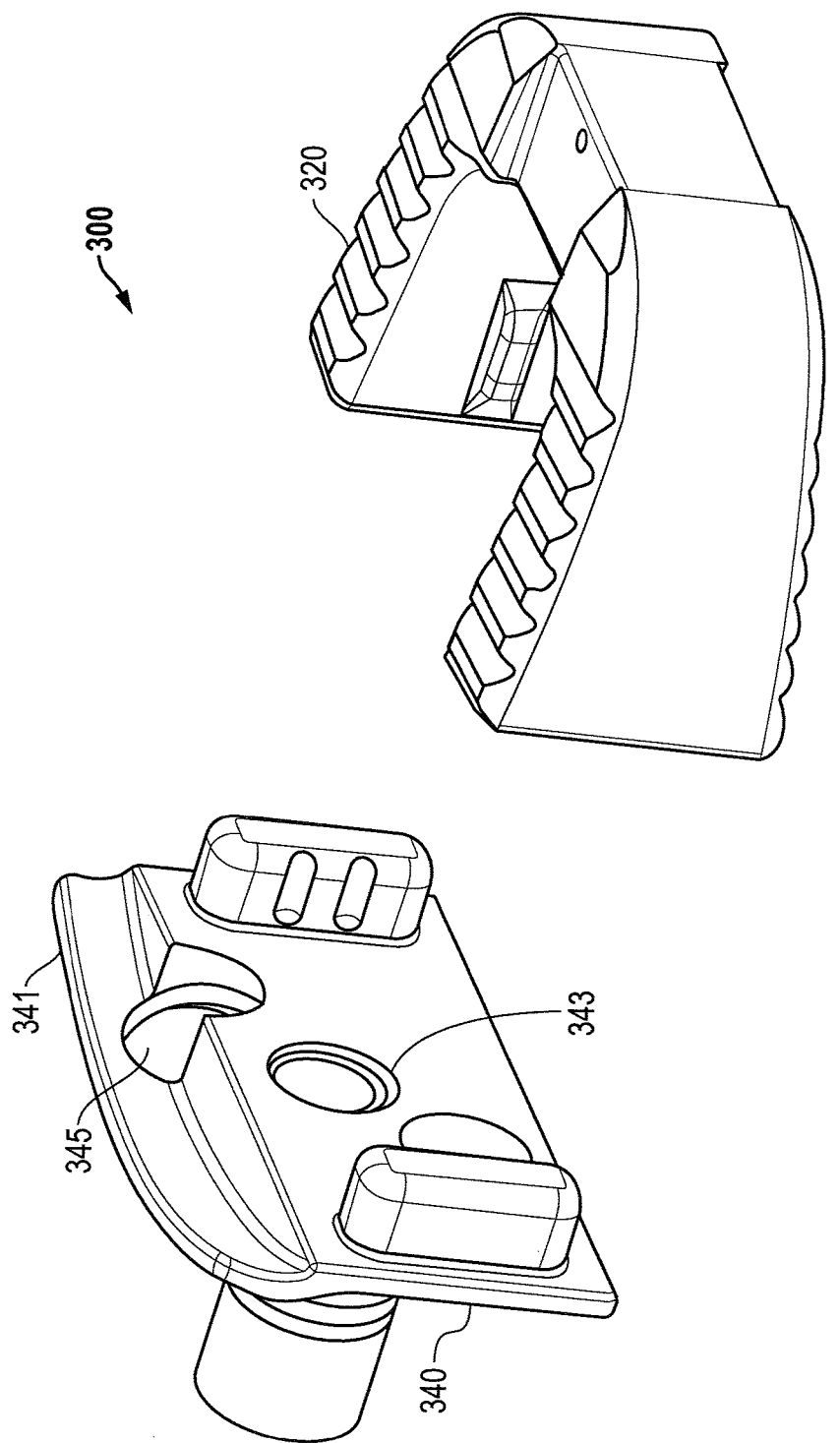
Figure 25:
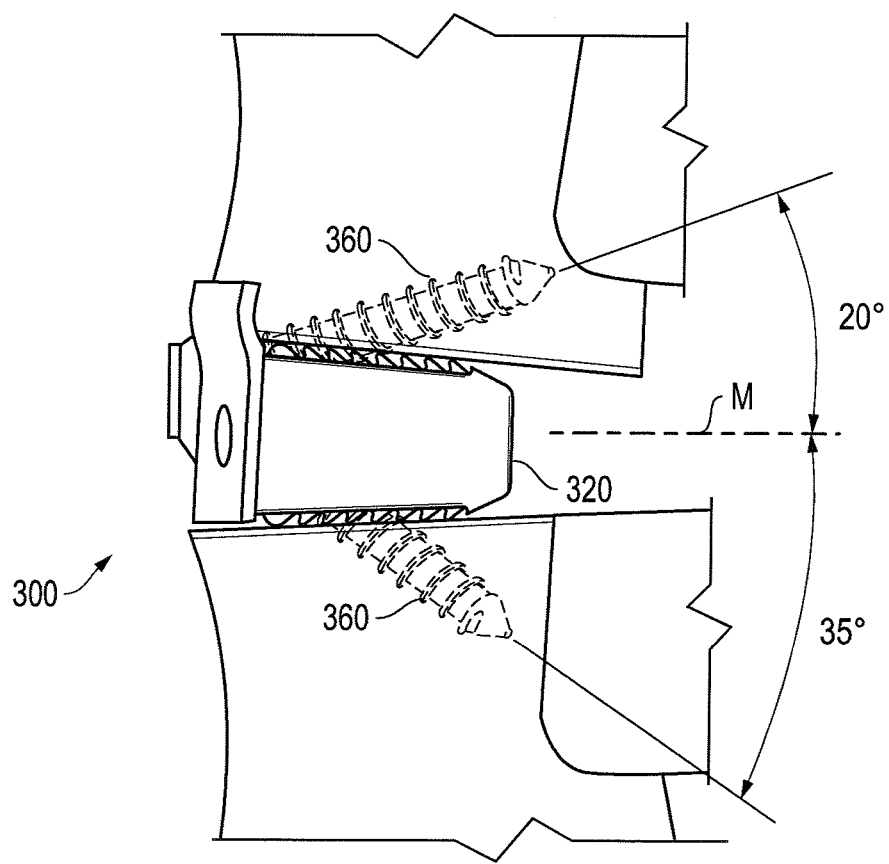

FIGS. 23-25 depict another spinal fusion device 300 similar to the embodiments of FIGS. 12-22, including a fusion component 320, an anterior retention component 340, two fasteners 360, and a locking mechanism 380, but which has a single lip 341 on the anterior retention plate 340. A single lipped anterior plate could be advantageously used such as when the given anatomy of a patient dissuades use of a dual lip configuration or when a dual lip configuration is simply not needed. For example, a bone shift or proximate to soft tissue may urge use of a single lip configuration. The single lip 341 abuts the apophyseal ring on either the upper or lower side. In FIGS. 23-25 the single lip 341 abuts the apophyseal ring of the upper vertebrae. In spinal fusion device 300, two bores are employed for receipt of the fasteners 360. Spinal fusion device 300 has zero profile on one side with the lip 341 (which can be referred to as a "chin") on the opposite side. The lip side, while not zero profile, has a low profile. As shown in FIG. 25, the configuration of the anterior plate 340 facilitates one fastener 360 to enter the upper vertebrae at approximately a 20 degree angle relative to the midline "M" of the device 300, whereas the lower fastener 360' enters the lower vertebrae at approximately a 35 degree angle.

Figure 26:
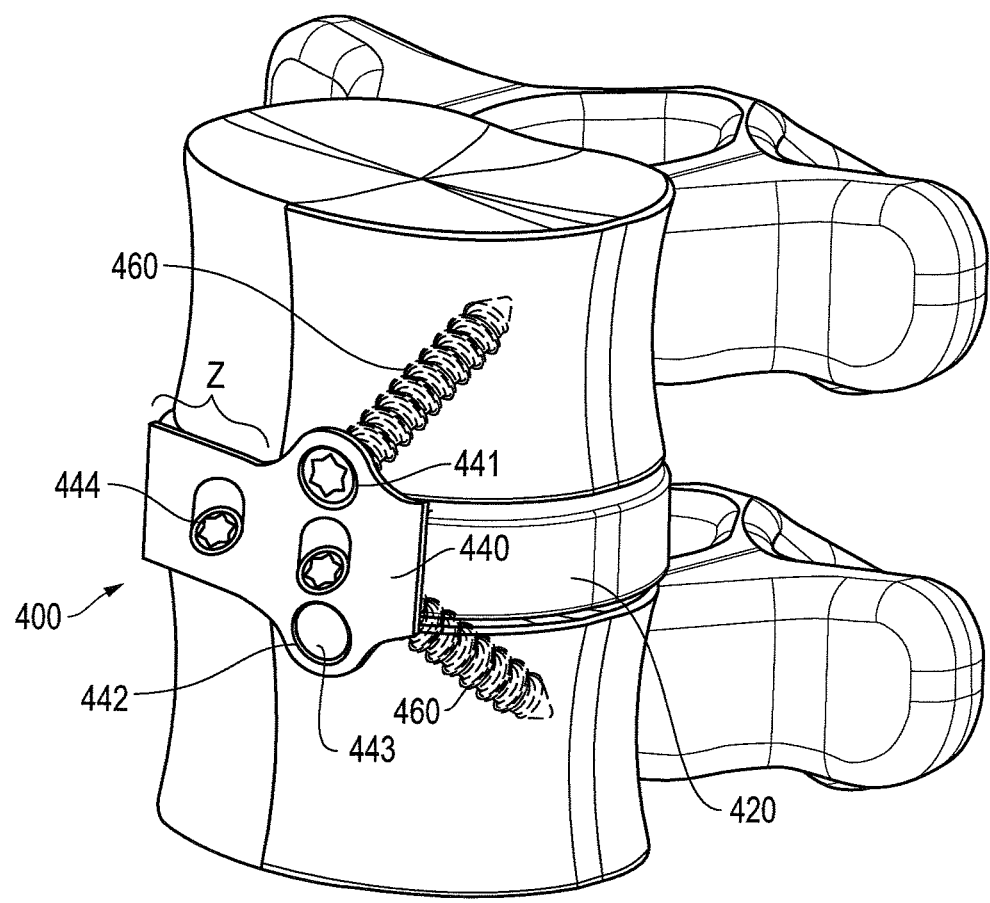
Figure 27:
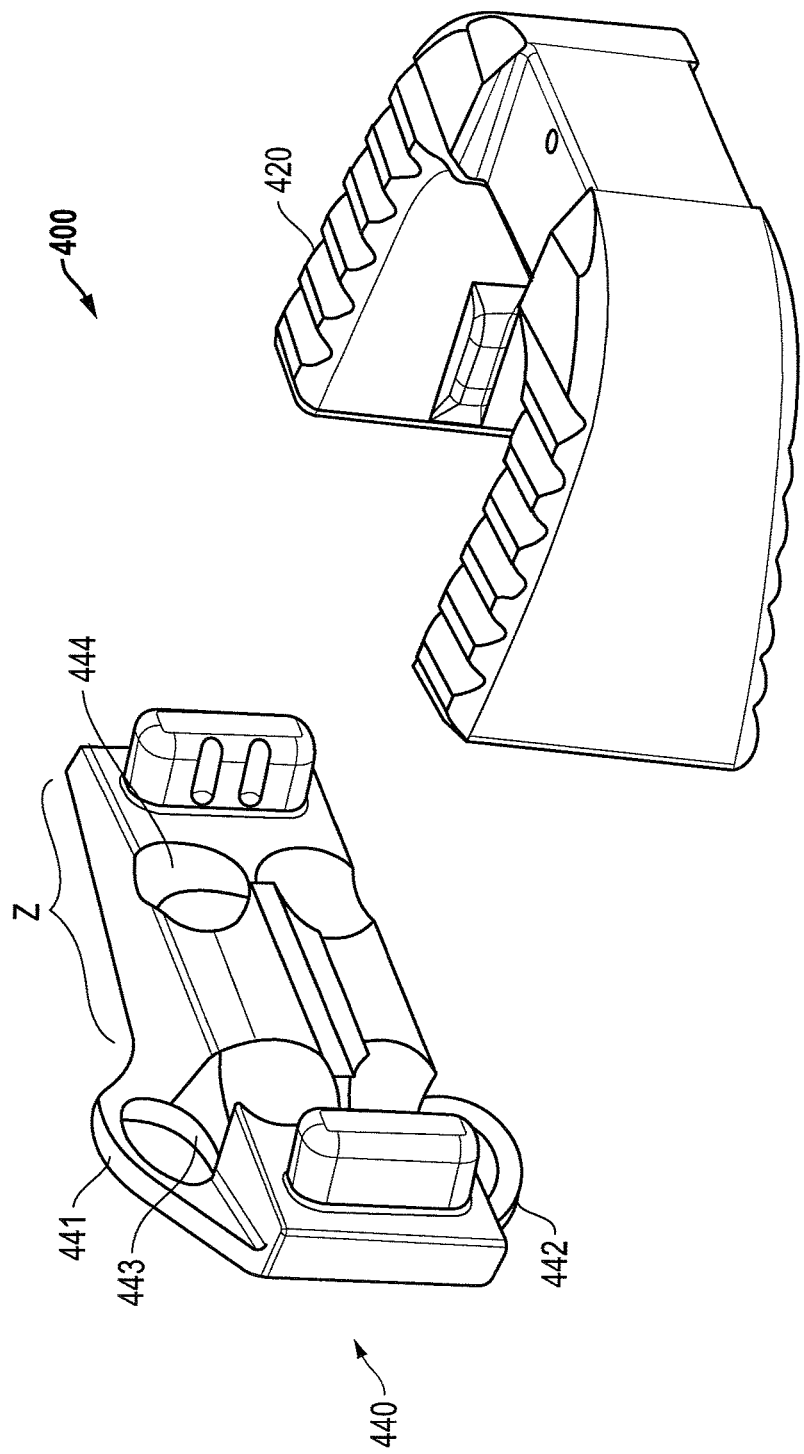
Figure 30:
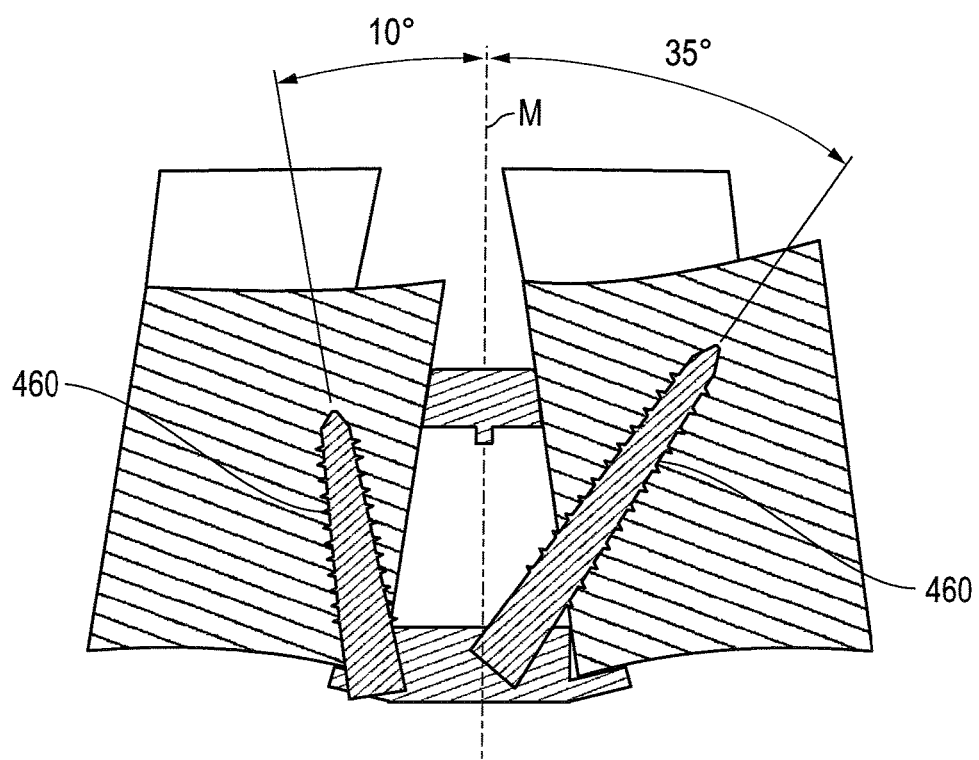

FIGS. 26-30 illustrate a spinal fusion device 400 that has a zero profile "Z" on approximately one-half of the anterior plate as one observes the device from left to right in FIG. 26, with the other half having lips 441, 442 that abut the apophyseal rings of both vertebrae. The lips 441, 442 include a portion of bores 443, 444 for receipt of fasteners. Like other embodiments herein, spinal fusion device 400 includes fusion component 420, anterior plate 440, and multiple fasteners 460. As seen in FIGS. 28-30, multiple bores 443, 444 provide for fastener placement at either about 10 degrees or 35 degrees, depending on the decision of the surgeon given the particulars of given vertebrae and fusion procedure. The embodiment of FIG. 26 can advantageously used as a means of bypass a bifurcated artery such as at L3-L4, for example, that is present that might interfere with the double or single lip preceding embodiments. This configuration permits reduced surface area on the lip, reversibility, and a mixed angles of approach (if desired).

Figure 31:
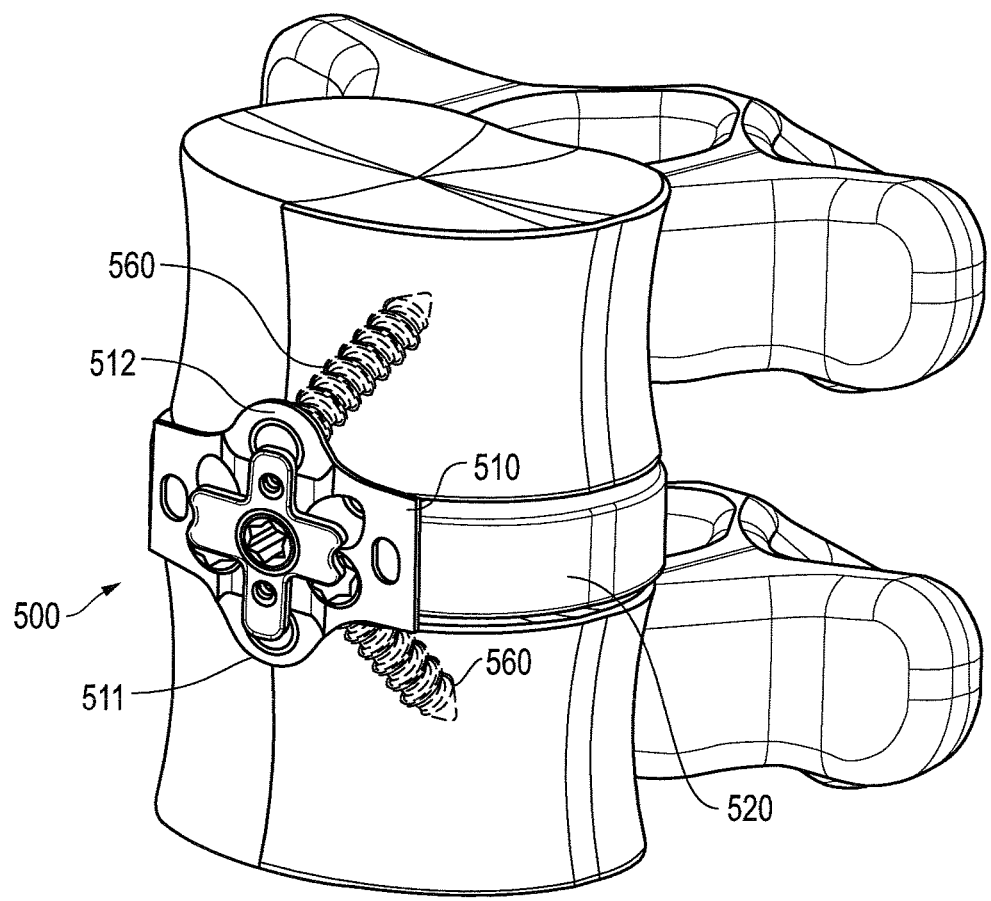
FIGS. 31 and 32 show an embodiment of the invention where the anterior plates has two centrally located lips on opposing side but wherein the plate is zero profile in the other portions of each opposing side
Figure 32:
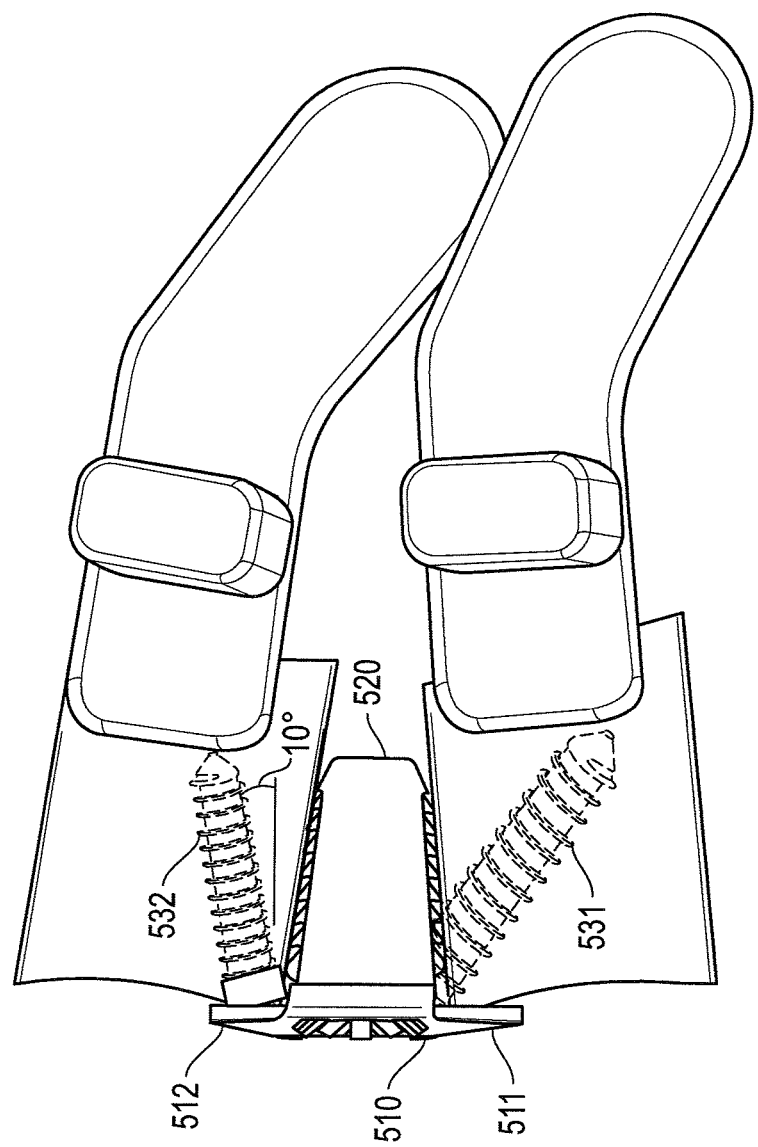

FIGS. 31 and 32 illustrate an embodiment similar to that shown in FIGS. 28 and 29, except the inferior and superior lips 511, 512 are positioned in the middle of the anterior plate 510. The device 500 can accommodate up to six fasteners. As shown in FIG. 32, the angle of approach into the vertebrae by the superior fastener 512 is about 10 degrees as measured from the center plane of the fusion component. The angle of approach of the inferior fastener 531 is about 35 degrees. Other angles could be used.

Each of the embodiments of FIGS. 12-32 has a low or minimal profile anteriorly. The locking mechanisms illustrated disclosed herein are not bound to any particular configuration and thus a given lock mechanism of a given embodiment in a FIG. can be used in other embodiments.

Following is an example of how an interbody fusion device of the present invention may be used in an ALIF spinal fusion procedure. As described above, a window is cut in the anterior side of the disc annulus 24 (FIG. 9) to allow an interbody fusion device to be inserted. Next, the nucleus pulpous 26 is cleaned out to provide room for the interbody fusion device. Next, a load bearing device 12 of the desired size (e.g., having a height to get the desired spacing between the vertebrae) is inserted between the end plates of the adjacent vertebrae using the appropriate instrumentation. During these procedures, the retention device 14 can be prepared with a desire material 60 placed in the hollow body 46. Once the surgeon is satisfied that the load bearing device is in the ideal position, the retention device 14 is inserted into the load bearing device 12, with the tongue 36 and groove 32 guiding the retention device 14. Note that, because the height of the retention device is less than the height of the load bearing device, the retention device 14 can slide into the load bearing device 12 without interfering with the relative placement of the load bearing device 12 and the end plates of the adjacent vertebrae. Also, the retention device 14 is stress shielded and is not axial loaded by the vertebrae. Once the retention device is in place, the bone screws 16 can be installed through the openings 48 and into the vertebrae. As the bone screws 16 are tightened, the vertebrae will compress vertebral bodies 20 and 22 onto the load bearing member 12, which will help facilitate fusion. Also, since the bone screws 16 secure the retention device 14, and do not directly secure the load bearing device 12, the bone screws will not tend to cause the interbody fusion device 10 to migrate. If desired, an anti-backout mechanism (such as the set screw 50 shown in FIG. 7) can be used to prevent the bone screws 16 from loosening.

The interbody fusion device of the present invention can be made from any desired materials. In one example, the load bearing device is made from PEEK (or a similar material), bone, metal, or any other structural substitute. In one example, the retention device is made from PEEK (or a similar material), bone, metal, or any other structural substitute. If the components of the interbody fusion device are radio-lucent (such as with PEEK), then doctors will be able monitor the fusion process better with X-rays.

An interbody fusion device of the present invention may be configured to any desired size or shape. In one example, load bearing devices can be provided in multiple thicknesses, allowing a surgeon to select a desired size (e.g., 10.5 mm, 12.5 mm, 14.5 mm, 16.5 mm, 1.5 mm, etc.). In the examples shown in the figures, the load bearing device has about 6° of lordosis (e.g., see FIG. 6). Of course any desired angle could be used.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

What is claimed is:

1. A spinal fusion device comprising:
   a U-shaped fusion component having two free ends and configured to have a zero profile when positioned between two adjacent vertebrae; and
   an anterior plate comprising:
      a body;
      a solitary upper lip portion extending from the body and offset toward a first side of the anterior plate;
      a solitary lower lip portion extending from the body and offset towards the first side of the anterior plate;
      a single first angled bore extending through both the body and the solitary upper lip portion; and
      a single second angled bore extending through both the body and the solitary lower lip portion;
   wherein the anterior plate is configured to have zero profile on approximately one half of the anterior plate and to couple to the U-shaped fusion component; and
   wherein a second side of the anterior plate that does not include the single angled bores has a height that is less than the height of the U-shaped fusion component so that, when positioned adjacent the vertebrae, the second side does not bear a load from a vertebra above the spinal fusion device and a vertebra below the spinal fusion device.

2. The spinal fusion device of claim 1, wherein the U-shaped fusion component is configured to generally conform to a contour of the adjacent vertebrae.

3. The spinal fusion device of claim 1, further comprising a first fastener and a second fastener, the first and second fasteners configured to couple to the single first bore and the single second angled bore, respectively.

4. The spinal fusion device of claim 3, wherein the first and second fasteners are bone screws.

5. The spinal fusion device of claim 1, wherein the U-shaped fusion component has a hollow center portion adapted to receive a material to enhance spinal fusion.

6. The spinal fusion device of claim 5, further comprising a protrusion formed on an inside wall of the U-shaped fusion component, the protrusion extending into the hollow center portion.

7. The spinal fusion device of claim 1, wherein the U-shaped fusion component and the anterior plate have a mating tongue and groove elements.

8. The spinal fusion device of claim 1, wherein the anterior plate is reversible so that the anterior plate can be used in two opposite configurations.

9. A method of fusing adjacent vertebrae, comprising:
   providing a spinal fusion device which comprises:
      a U-shaped fusion component having two free ends and configured to have a zero profile when positioned between two adjacent vertebrae, the U-shaped fusion component having a hollow center portion between the two free ends that is configured to receive a material to enhance spinal fusion;
      an anterior plate comprising:
      a body;
      a solitary upper lip portion extending from the body and offset toward a first side of the anterior plate;
      a solitary lower lip portion extending from the body and offset towards the first side of the anterior plate;
      a single first angled bore extending through both the body and the solitary upper lip portion; and
      a single second angled bore extending through both the body and the solitary lower lip portion;
      a first fastener and a second fastener, the first and second fasteners configured to couple to the single first and second angled bores, respectively;
      wherein the anterior plate is configured to have zero profile on approximately one half of the anterior plate and to couple to the U-shaped fusion component; and
      wherein a second side of the anterior plate that does not include the single angled bores has a height that is less than the height of the U-shaped fusion component so that the second side does not bear a load from a vertebra above the spinal fusion device and a vertebra below the spinal fusion device;

inserting the U-shaped fusion component between two adjacent vertebrae;

coupling the anterior plate to the U-shaped fusion component; and driving the first and second fasteners into the vertebrae through the single first and single second angled bores, respectively, to secure the anterior plate to the U-shaped fusion component and to pull the vertebrae toward the anterior plate and the spinal fusion device.

10. The method of claim 9, wherein bone graft material is packed in the hollow center portion prior to coupling.

11. The method of claim 9, further comprising a protrusion formed on an inside wall of the U-shaped fusion component, the protrusion extending into the hollow center portion.

\* \* \* \* \*